United States Patent
Murphy

[19]

[11] Patent Number: 5,851,220
[45] Date of Patent: Dec. 22, 1998

[54] SYSTEM AND METHOD FOR AUTOMATIC ADJUSTMENT OF SHOCK PARAMETERS

[75] Inventor: Anthony J. Murphy, Dulwich Hill, Australia

[73] Assignee: Pacesetter, Inc., Sylmar, Calif.

[21] Appl. No.: 978,248

[22] Filed: Nov. 25, 1997

[51] Int. Cl.⁶ .................................................. A61N 1/39
[52] U.S. Cl. .................................................. 607/5
[58] Field of Search ............................. 607/4–8, 14

[56] References Cited

U.S. PATENT DOCUMENTS

| | | | |
|---|---|---|---|
| 3,805,795 | 4/1974 | Denniston et al. | 607/6 |
| 4,181,133 | 1/1980 | Kolenik et al. | 607/14 |
| 5,224,475 | 7/1993 | Berg et al. | 128/419 |
| 5,344,430 | 9/1994 | Berg et al. | 607/8 |
| 5,395,373 | 3/1995 | Dyers | 607/5 |
| 5,489,293 | 2/1996 | Pless et al. | 607/5 |

*Primary Examiner*—William E. Kamm
*Attorney, Agent, or Firm*—Gottlieb, Rackman & Reisman, P.C.

[57] ABSTRACT

An implantable defibrillator generates defibrillation shocks for providing antitachycardia therapy. The shocks have an intensity, i.e. amplitude and/or duration, which is dynamically changed in accordance with whether defibrillation shocks having a particular intensity are successful or not. In this manner, changes either in the cardiac condition or the interface between the defibrillation electrodes and the cardiac tissues, or other causes which may have an effect on the effectiveness of the defibrillation shocks.

16 Claims, 3 Drawing Sheets

SYSTEM AND METHOD FOR AUTOMATIC ADJUSTMENT OF SHOCK PARAMETERS

BACKGROUND OF THE INVENTION

A. Field of Invention

This invention pertains to implantable cardioverter defibrillators (ICDs) used to apply therapeutic shocks to patients suffering from tachyarrhythmia, and more particularly to an ICD which automatically adjusts the parameters of such therapeutic shocks.

B. Description of the Prior Art

Defibrillators form a part of implantable ICDs used to apply antitachyarrhythmic therapy to a patient. Typically, ICDs contain a defibrillator system and a pacemaker system. A typical implantable pacemaker is coupled to one or more electrodes extending into the patient's heart. The pacemaker includes sensors for sensing intrinsic activity in the patient's heart, one or more pacing generators for generating pacing pulses to one or both chambers of the heart on demand and a controller (which is typically a microprocessor) used to analyzed the signals sensed in the heart chamber by the sensors and in response, generate command signals to the pacing generator(s) for generating appropriate pacing pulses. This arrangement is suitable for applying antibradycardia therapy as well as antitachycardia pacing therapy.

An ICD typically includes all the elements described above, and in addition, also includes a high voltage section for generating high voltage defibrillation shocks, which typically are delivered through one or more separate defibrillator electrodes.

One of the parameters programmed for the defibrillator is the intensity of the defibrillation shocks, i.e. the maximum amplitude as well as the duration of each shock. Because of individual cardiac characteristics of patients, the optimal shock intensity for each patient is different. In order to determine what is an operative intensity, typically, after implantation, the clinician programs the device for defibrillation shocks of a particular intensity, based on recommendations by the manufacturer, his experience, the age and health of the patient and other factors. He then induces fibrillation in the patient, and checks to see if the defibrillator is able to revert the heart to a sinus rhythm. In order to insure that proper defibrillation shocks are generated in the future, the clinician typically selects a shock intensity which has an increased safety margin, that is, the defibrillation shock will have a 50–100% higher peak amplitude than the threshold value necessary for the defibrillation shock to be effective. The width of the defibrillation pulse also affects the intensity, though typically this parameter is left at a nominal value of around 4 msec.

A major problem with this process of selecting the defibrillation shock intensity is that all ICDs and pacemakers obtain energy from a battery. Since the devices are substantially permanently implanted, this battery must have sufficient capacity (i.e. useful life) to power to device for a long time period, such as 5–10 years. However, because of the safety margin programmed for the defibrillation shock intensity, each time defibrillation shocks are applied, unnecessary energy is wasted because this intensity is higher than necessary. Accordingly, during each fibrillation episode, the capacity of the battery is reduced needlessly. The process of testing to determine the defibrillation threshold further reduces the battery capacity. The testing creates additional trauma for the patient, and makes the procedure longer and therefore more expensive.

A further problem with the existing process is that it ignores physiological or bioelectrical changes in the patient. As time goes by, the patient's cardiac characteristic may change sufficiently so that to be effective the defibrillation shocks must have either a higher intensity, or could have a lower intensity. Additionally, the interface between the defibrillation electrode(s) and the cardiac tissue changes as well, resulting in a corresponding change in the electrode/tissue impedance. This change also affects the efficacy of the defibrillation shocks.

Methods and apparatus for terminating VT and VF in a patient with multiple defibrillation pathways is disclosed in U.S. Pat. Nos. 5,344,430 and 5,224,475.

OBJECTIVES AND SUMMARY OF THE INVENTION

In view of the above-mentioned disadvantages of the prior art, it is an objective of the present invention to provide a defibrillator device for delivering defibrillation shocks which automatically adapts to changes in either or both physiological changes in the patient's heart and the interface between the defibrillation electrode and the cardiac tissues.

A further objective is to provide a device which automatically determines if defibrillation shocks are effective, and increases their intensity if they are found to be ineffective.

A further objective is to provide a device which automatically determines if the defibrillation shocks have a higher intensity than necessary and automatically decreases said intensity.

Other objectives and advantages of the invention shall become apparent from the following description of the invention.

Briefly, an ICD constructed in accordance with this invention, includes a sensor for sensing intrinsic activity in the heart, a pacing generator for generating pacing pulses on demand in response to pacing commands, a defibrillator for generating defibrillation shocks in response to defibrillation commands and a controller receiving signals indicative of said intrinsic activity and generating in response said pacing and defibrillation commands. Importantly the ICD also includes a defibrillation control module which is preferably incorporated into said controller and which monitors and determines the optimal intensity of the defibrillation shocks in accordance with predetermined criteria.

More specifically, using past history, the defibrillator controller determines if the current intensity for defibrillation shocks is too low or insufficient. In response the current intensity is increased. Alternatively, if the current intensity appears to be too high, for example, because the shocks are almost always successful. In this case the current value is decreased.

DETAILED DESCRIPTION OF THE INVENTION

Figure 1:
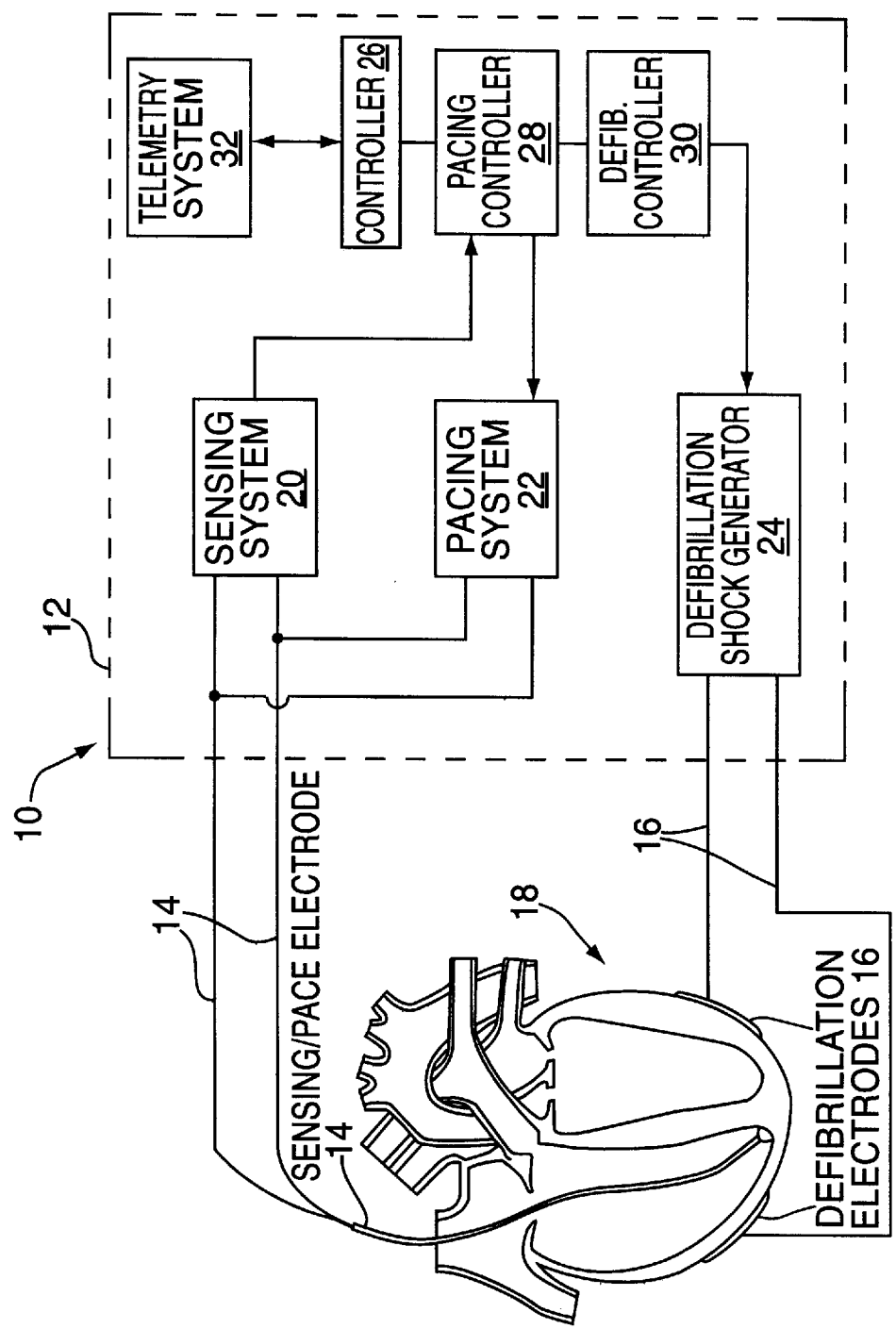
FIG. 1 shows a block diagram of a ICD constructed in accordance with this invention.

Referring first to FIG. 1, a cardioversion device 10 constructed in accordance with this invention includes an implantable housing 12, a set of pacing/sensing electrodes 14 and one or more defibrillation electrodes 16, said electrodes extending to the heart 18 of a patient after implantation.

Within housing 12 there is provided sensing system 20, a pacing system 22, a defibrillation shock generator 24 and a controller 26. For the purposes of this invention, the controller 26 is shown as having two components: a pacing controller 28 and a defibrillation controller 30, it being understood that these components are best implemented in a single microprocessor.

Communication with an external programmer or other interface device is accomplished through a telemetry system 32.

Briefly, intrinsic cardiac activity within the heart 18 is sensed by sense system 20 through electrodes 14. The sense system then generates sense signals corresponding to this activity to pacing controller 28. The pacing controller than makes a determination of the status of the heart, i.e., whether it is operating at a sinus rate, or whether it is arrhythmic. If the heart is arrhythmic, i.e. its rate indicates either bradycardia or a ventricular tachycardia, the pacing controller 26 generates commands to the pacing system 22 to apply pacing pulses and thereby provide either antibradycardia or antitachycardia pacing therapy. For fibrillation, the defibrillation controller 30 generates defibrillation commands. In response, as described more fully below, the defibrillation controller 30 sends commands to the defibrillation shock generator 24 which define the intensity of the defibrillation shocks, i.e., the duration and maximum amplitude of each shock, as well as timing information to synchronize the defibrillation pulses to the intrinsic cardiac activity as indicated by the sense signals form sense system 20.

Figure 2:
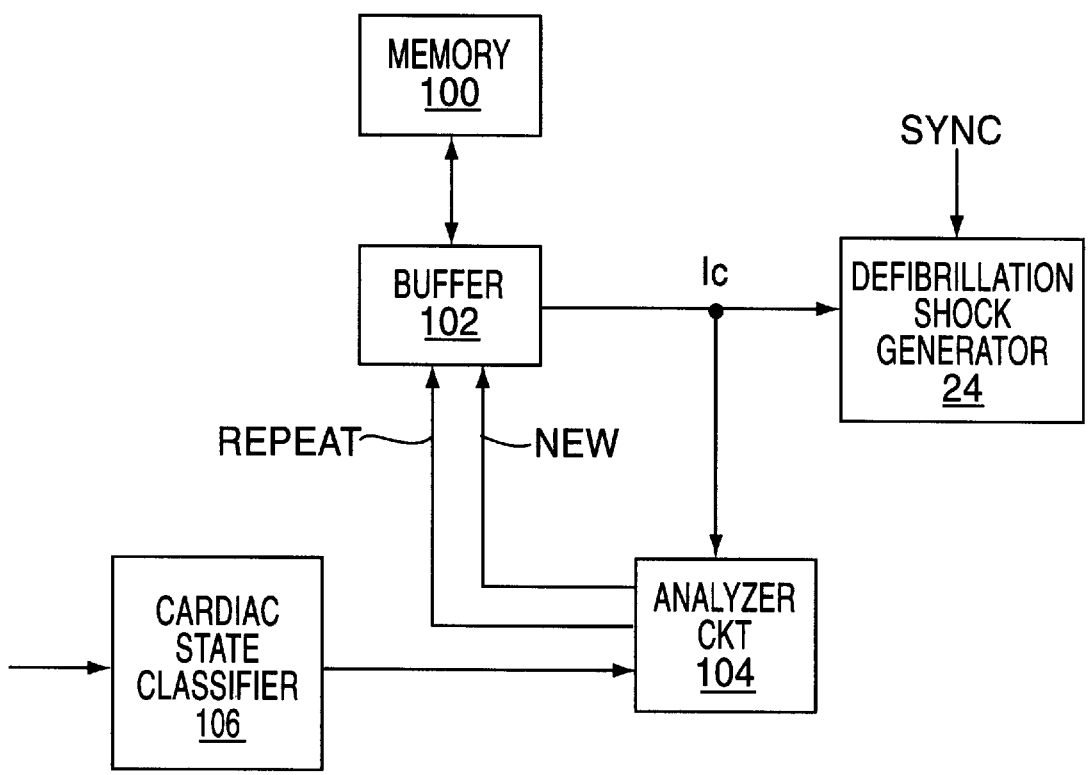
FIG. 2 shows a block diagram for the defibrillator control module.

More specifically, as shown in FIG. 2, the defibrillation controller 28 includes a memory 100, a buffer 102, and an analyzer circuit 104. Also provided is a cardiac state classifier 106 which is preferably disposed or is part of the pacing controller 28. Classifier 106 uses various information for example the sense signals from the sense system 20 to determine the status of heart 18.

The memory 100 is used to hold the current or latest intensity Ic for the defibrillation shocks being applied as well as the success or failure of shocks associated with M previous fibrillation episodes of the patient. As previously mentioned intensity command Ic defines a peak amplitude and a duration for each defibrillation shock.

In the discussions above, for the sake of simplicity it was assumed that during each fibrillation episode, either one defibrillation shock is applied, or that several shocks are applied having the same identical characteristics. However, it is preferable that during each fibrillation episode, several shocks be applied, with the first shock having the characteristics defined by intensity command Ic and each subsequent shock being defined in a predetermined manner. For instance, the second shock may have an intensity 50% higher than the first shock. The third, and all subsequent shocks (if any) may have a preset maximum intensity. Thus, the discussion of shock intensities for shocks of different episodes refers to the characteristics of the first shock in each fibrillation episode.

The current intensity Ic is also loaded into a buffer 102 which then transmits it to the generator 24.

A SYNC signal is generated by a timer (not shown) within pacing controller 28. The purpose of this SYNC signal is to insure that the defibrillation shocks are delivered at a preselected interval during a particular QRS complex of the heart.

The defibrillation shock generator 24 charges one or more capacitors (not shown) to a voltage level related to the intensity command Ic. When the SYNC signal is received the capacitors are discharged to produce the defibrillation shocks.

The intensity Ic is also delivered to the analyzer circuit 104.

Figure 3:
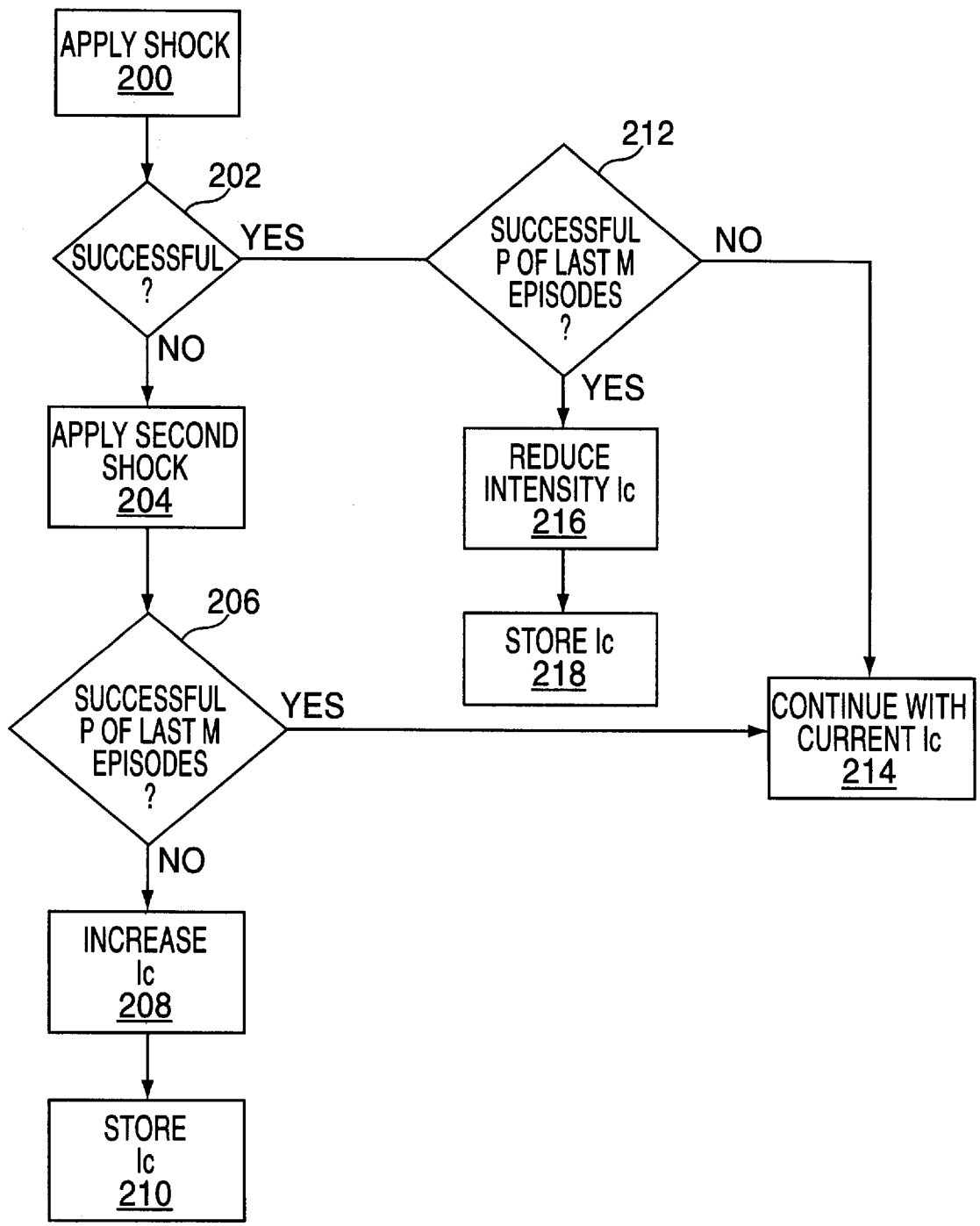
FIG. 3 shows a flow chart for the operation of the subject cardioversion device.

For a better understanding of the invention, reference is now made to FIG. 3 which shows a flow chart for the block diagram of FIG. 2.

Starting at step 200, a fibrillation episode is detected by the controller 28 and the current intensity Ic is sent to the generator 24. The generator 24 then generates a defibrillation shock having the characteristics designated by Ic. At the beginning of the operation of the device 10, i.e. after initial programming, Ic has an initial or default value preprogrammed into the memory 100 or determined by the clinician. The value of Ic is then adaptively adjusted in accordance with the present invention as follows.

In step 202 the analyzer circuit 104 monitors the output of status indicator circuit 102. If a fibrillation is not reverted by the first shock, that means that the latest defibrillation shock was unsuccessful. Therefore in step 204 the analyzer 104 sends a REPEAT command to the buffer 102 to request a second defibrillation shock. This second shock may have the same or a higher intensity IC+ than the current intensity Ic.

In one embodiment of the invention the analyzer circuit 104 also sends a command to buffer 102 to increase the intensity by a predetermined amount. Therefore either the repeated shock or during the next fibrillation episode, the defibrillation shock will have a higher intensity.

However, preferably, rather than increasing the value of Ic immediately, the analyzer 104 can perform in step 206 a test to determine how often during the last M fibrillation episodes did the fibrillation shock with intensity Ic fail. The analyzer 104 decides in this embodiment to increase Ic only if certain criteria are met. One such criteria would be, for example, if during at least N of the last M fibrillation episodes, shocks with intensity Ic failed to revert the heart. One value for N/M could for example 10%.

In step 206 if the criteria is met then it is assumed that for some reason the current intensity Ic is insufficient. Therefore in step 208 the current intensity in the buffer 102 is increased by an incremental amount(step 208). This value Ic+ is stored in buffer 102 and memory 100 (step 210) together with information identifying the current fibrillation episode so that during the next fibrillation episode a higher intensity shock is used.

Returning to step 202, if the last shock is successful then in step 212 a determination is made as to whether the current intensity Ic is unnecessarily high. For example, a determination can be made based on information from memory 100 whether at least P shocks for the last M episodes at intensity Ic were successful. For this test P/M could be 90%. If not then in step 214 normal operation continues using Ic as the intensity for the next shock.

If the intensity Ic is unnecessarily high as determined by the test of step 212, then in step 216 the intensity is reduced by an incremental amount. This new value is stored in buffer 102. The new value is also stored in memory together with information identifying the current fibrillation episode (step 218). Therefore during the following fibrillation episode a lower intensity shock is used.

In this manner, over time, the defibrillator controller automatically adapts itself to the condition of the patient, the electrodes, and so on, and insures in this manner that the defibrillation shocks applied to the patient have an optimum intensity.

Although the invention was described with reference to several particular embodiments, it is to be understood that these embodiments are merely illustrative of the application of the principles of the invention. Accordingly, the embodiments described in particular should be considered exemplary, not limiting, with respect to the following claims.

I claim:

1. An implantable defibrillator device comprising:
   a defibrillation shock generator for generating defibrillation shocks, said defibrillation shocks having an intensity, said intensity being defined by a command;
   a sensor for sensing if a plurality of defibrillation shocks for different fibrillation episodes were successful and generating a corresponding success rate;
   a controller for generating said command, said controller being adapted to adjust said intensity based on said success rate.

2. The device of claim 1 wherein said controller is adapted to adjust said intensity upward if said success rate level falls below a predetermined level.

3. The device of claim 1 wherein said controller is adapted to adjust said intensity downward if said success rate exceeds another predetermined threshold.

4. The device of claim 1 further comprising a memory for storing said intensity.

5. A method of dynamically adjusting the intensity of defibrillation shocks delivered by an implantable cardiac defibrillator, said method comprising the steps of:
   sensing a fibrillation episode;
   applying a defibrillation shock to a patient's heart in the presence of said fibrillation episodes, said defibrillation shock having a first intensity;
   determining if several previous defibrillation shocks of said first intensity were successful in reverting said heart to a normal sinus rhythm; and
   changing said intensity based on said determination.

6. A method of dynamically adjusting the intensity of defibrillation shocks delivered by an implantable cardiac defibrillation, said method comprising the steps of:
   sensing a first fibrillation episode;
   applying a first defibrillation shock to a patient's heart, said first shock having a first intensity;
   determining if a plurality of previous shocks including said first shock were successful;
   changing said intensity downward if a first predetermined number of said plurality of previous shocks were determined to be successful;
   determining if another plurality of previous shocks were unsuccessful; and
   changing said intensity upward if said another plurality is determined to be unsuccessful.

7. The method of claim 6 wherein said another plurality of previous shocks is determined to be unsuccessful if out of a total of M shocks, P shocks did not result in reversion of the heart from a tachycardia condition to a normal sinus rhythm.

8. The method of claim 7 wherein said another plurality of previous shocks is determined to be unsuccessful if out of a total of M shocks, P shocks did not result in reversion of the heart from a tachycardia condition to a normal sinus rhythm.

9. The method of claim 6 further comprising
   defining a ratio N/M wherein M is the number of shocks that resulted in reversion out of N episodes;
   comparing said ratio to a first threshold; and
   decreasing said intensity if said ratio is larger than a first threshold.

10. The method of claim 6 further comprising
    defining a ratio N/M wherein M is the number of shocks that resulted in reversion out of N episodes;
    comparing said ratio to a second threshold; and
    increasing said intensity if said ratio is smaller than a second threshold.

11. An implantable cardioversion device for providing antiarrhythmia therapy to a patient's heart comprising:
    a sensing system that senses cardiac activity in a patient's heart and generates corresponding sense signals;
    a classifier circuit which receives said sense signals and identifies a tachycardia episode based on said sense signals;
    a controller coupled to said classifier circuit that generates corresponding command signals, said command signals defining said antiarrhythmia therapy corresponding to said tachycardia episode;
    a pulse generator that receives said command signals and generates pulses selected for antiatachycardia therapy when said tachycardia episode has been identified, said pulses having an intensity defined by said command signals; and
    an analyzer circuit coupled to said sensing system and said controller to analyze whether pulses associated with previous tachycardia episodes have successfully reverted said patient's heart to a normal sinus rhythm and generating a corresponding intensity change signal;
    wherein said controller circuit is adapted to modify said command signals to change said intensity in accordance with said intensity change signal.

12. The device of claim 11 wherein said analyzer circuit is adapted to analyze said pulses by correlating the result of pulses responsive to at least two episodes.

13. The device of claim 11 wherein said analyzer circuit is adapted to determine a success ratio defined by a number of successfully reverted tachycardia episodes and a total number of tachycardia episodes.

14. The device of claim 13 further comprising a comparator that compares said ratio to a first threshold level, and wherein said intensity change signal indicates an increase in said intensity if said ratio is below said first threshold level.

15. The device of claim 13 wherein said comparator further compares said ratio to a second threshold level, wherein said intensity change signal indicates a decrease in said intensity of said ratio is above said second threshold level.

16. The device of claim 11 wherein said classifier is adapted to sense a fibrillation episode, and said pulse generator generates defibrillation shock pulses in the presence of said fibrillation episode.

* * * * *